United States Patent
Lim et al.

Patent Number: 6,074,438
Date of Patent: *Jun. 13, 2000

[54] HAIR DYEING COMPOSITIONS CONTAINING 2-CHLORO- AND 2,6-DICHLORO-4-AMINOPHENOL AND PHENYLPYRAZOLONES

[75] Inventors: Mu-Ill Lim, Trumbull; Yuh-Guo Pan, Stamford; Linas R. Stasaitis, Fairfield, all of Conn.

[73] Assignee: Bristol-Myers Squibb Co., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/033,632

[22] Filed: Mar. 3, 1998

[51] Int. Cl.$^7$ .................................................. A61K 7/13
[52] U.S. Cl. ........................... 8/409; 8/408; 8/421; 8/423
[58] Field of Search ............................... 8/406, 408, 409, 8/410, 411, 412, 421, 423

[56] References Cited

U.S. PATENT DOCUMENTS

| | | | |
|---|---|---|---|
| 3,413,072 | 11/1968 | Ghilardi et al. | 8/421 |
| 3,506,389 | 4/1970 | Charle et al. | 8/409 |
| 3,820,948 | 6/1974 | Berth | 8/409 |
| 3,918,896 | 11/1975 | Kalopissis et al. | 8/409 |

(List continued on next page.)

FOREIGN PATENT DOCUMENTS

| | | | |
|---|---|---|---|
| 756849 | 3/1971 | Belgium . | |
| 79540 | 5/1983 | European Pat. Off. . | |
| 0410471 | 1/1991 | European Pat. Off. | C07C 217/84 |
| 0446132 | 3/1991 | European Pat. Off. | A61K 7/13 |
| 0459900 | 5/1991 | European Pat. Off. | A61K 7/13 |
| 0465339 | 7/1991 | European Pat. Off. | A61K 7/13 |
| 0465340 | 7/1991 | European Pat. Off. | A61K 7/13 |
| 0605320 | 12/1993 | European Pat. Off. | A61K 7/13 |
| 0377288 | 6/1923 | Germany . | |
| 377288 | 6/1923 | Germany . | |
| 2160318 | 6/1973 | Germany . | |
| 2357215 | 5/1975 | Germany | A61K 7/13 |
| 3145141 | 5/1983 | Germany | A61K 7/13 |

OTHER PUBLICATIONS

CAPLUS Abstract of ZA 6802753, Berth, Nov. 1968.
Bull. Soc. Chim. Fr. (1994) pp. 291–293, Anceau et al, "Stéréosélectiveitiés comparées des réactions d'alkylation et d'aldolisation d'énolates deγ–valérolactones. " (no month available).

Primary Examiner—Caroline D. Liott
Attorney, Agent, or Firm—Charles J. Zeller; Morton S. Simon

[57] ABSTRACT

The invention provides compositions and methods for the oxidative coloring of human hair. The compositions of the invention contain as a primary intermediate at least one aminophenol of the formulas:

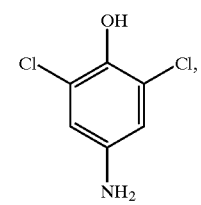

(1)

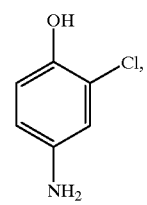

(2)

or a cosmetically acceptable salt thereof, and at least one pyrazolone coupler of the formulas:

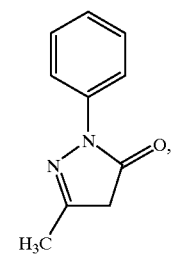

(3)

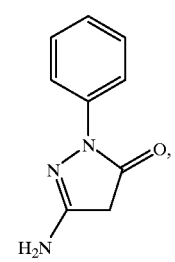

(4)

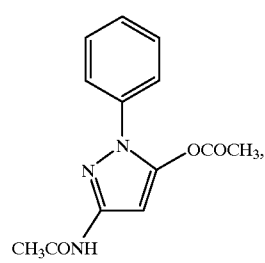

(5)

or a cosmetically acceptable salt thereof. The compositions may also contain one or more other primary intermediates and conventional coupling compounds, in addition to an oxidizing agent and other components typically used in oxidative hair dye preparations.

25 Claims, No Drawings

U.S. PATENT DOCUMENTS

| | | | |
|---|---|---|---|
| 3,948,596 | 4/1976 | Kalopissis et al. | 8/409 |
| 4,003,699 | 1/1977 | Rose et al. | 8/409 |
| 4,169,703 | 10/1979 | Fakhouri | 8/421 |
| 4,212,645 | 7/1980 | Leon et al. | 8/406 |
| 4,289,495 | 9/1981 | Bugaut et al. | 8/406 |
| 4,425,132 | 1/1984 | Grollier et al. | 8/406 |
| 4,470,826 | 9/1984 | Bugaut et al. | 8/406 |
| 4,566,875 | 1/1986 | Grollier et al. | 8/406 |
| 4,727,192 | 2/1988 | Junino et al. | 8/410 |
| 4,863,480 | 9/1989 | Bugaut et al. | 8/408 |
| 4,904,275 | 2/1990 | Grollier et al. | 8/408 |
| 5,015,260 | 5/1991 | Tamura et al. | 8/408 |
| 5,047,066 | 9/1991 | Mano et al. | 8/421 |
| 5,104,414 | 4/1992 | Tamura et al. | 8/408 |
| 5,279,520 | 1/1994 | Junino et al. | 8/409 |
| 5,540,738 | 7/1996 | Chan et al. | 8/406 |

HAIR DYEING COMPOSITIONS CONTAINING 2-CHLORO- AND 2,6-DICHLORO-4-AMINOPHENOL AND PHENYLPYRAZOLONES

FIELD OF THE INVENTION

The invention relates generally to methods and compositions for preparing stable oxidative hair dyes that result in long lasting and true colors. Thepresent invention more particularly relates to oxidative hair dye compositions and methods comprising particular aminophenols and phenylpyrazolones in addition to other conventionally-used additives and components.

BACKGROUND OF THE INVENTION

Oxidative hair dye colorants are essential elements in hair dyeing preparations for the permanent dyeing of human hair. The hair dyeing process is achieved, in general, by the reaction of certain developing compounds with certain coupling compounds in the presence of a suitable oxidizing agent or compound, such as hydrogen peroxide.

When oxidation dye precursors such as those comprising primary intermediates and couplers are used in the dyeing of human hair, the procedure may involve the use of a two part system. In general, one part can be a formulation which contains a variety of ingredients, including oxidation dye precursors (i.e., primary intermediates and coupling agents). The other part is a developer formulation containing a suitable oxidizing agent, e.g., hydrogen peroxide. Immediately prior to application to the hair, the two parts are mixed to form a thickened liquid solution, for example, a lotion or a gel. As a consequence of the oxidizing properties of the oxidizing agent, some of the natural melanin pigment of the hair may be bleached. The dye precursors in the thickened solution (e.g., lotion or gel) penetrate into the hair and the primary intermediates are oxidized and react with coupling agents to produce the desired color. Such systems generally contain a proportion of organic solvents and surfactants and contain relatively high levels of dye precursors to produce the desired color.

In order for procedures using permanent oxidative dyes to work properly, a number of parameters and conditions are important to consider in the use of the permanent oxidative dye intermediates in admixture with couplers in hair color preparations for human hair. Among these are the final color and color intensity that are produced after application to the subject's hair; the wash fastness and the light fastness of the resulting dye; the resistance of the dye to perspiration; the resistance of the dye to various hair treatments, such as permanent wave, straightening, shampooing, conditioning and rubbing. In addition, the dye must have virtually no allergenicity or dermal or systemic toxicity.

p-Phenylenediamine (PPD) plays a very important role in oxidative hair coloring because a majority of shades are obtained with dyes based on this compound. The hair coloring industry is searching for a p-phenylenediamine alternative which possesses a better allergenic profile than p-phenylenediamine.

German Patent 377,288 (1923) discloses that coupling 4-amino-2,6-dichlorophenol with 2,4-diaminoanisole dyed hair blue black. German Patent 3,145,141 discloses oxidative dyeing compositions containing 4-amino-2,6-dichlorophenol, as the developer, and at least one of 1-naphthol, 1,5-dihydroxynaphthalene, m-aminophenol and N,N-bis(2-hydroxyethyl)-m-phenylenediamine, as the coupler. These compositions provide deep blue to black blue colorations which do not change when subjected to permanent waving treatments using thioglycolate or sulfite.

4-Amino-2-chlorophenol has been frequently mentioned as a part of extensive list of 4-aminophenol derivatives as a primary intermediate in patents on hair coloring. However, the usefulness of this compound has not been demonstrated in the prior art. Prior art references which mention 4-amino-2-chlorophenol include:

U.S. Pat. No. 5,540,738 which relates to single-stage oxidative hair coloring compositions containing iodide, oxidant and oxidative dye;

EP 605,320 A1 which discloses oxidative hair dye compositions containing paraphenylenediamines, metaphenylenediamines, and benzimidazole derivatives;

EP 465,340 A1 which teaches acidic oxidative hair dye containing 4-hydroxyindole;

EP 465,339 A1 which relates to acidic oxidative hair dye containing 4-hydroxyindole;

EP 459,900 A1 which discloses hair dye preparations containing 2,4-diamino-1,3-dimethoxybenzene as a coupling agent in acidic medium;

EP 446,132 A1 which teaches a process for dyeing keratinous fibers with 6- or 7-monohydroxyindoles at acidic pH; and EP 410,471 A2 which relates to aminophenols, nitrophenol intermediates and their preparation, and hair-dyeing compositions containing as couplers.

1-Phenyl-2-pyrazolin-5-one has also been mentioned in prior art patents.

GB 2,168,727 A describes a dyeing composition for keratinous fibers, and especially for human hair. The composition contains at least one oxidation dye precursor and at least one water-soluble bio-heteropolysaccharide and an oxidizing agent. 3-Methyl-1-phenyl-2-pyrazolin-5-one is mentioned among many couplers.

U.S. Pat. No. 4,212,645 covers hair dyeing compositions containing an aryldiamine and a substituted catechol. Substituted catechol derivatives together with p-phenylediamine derivatives can be employed to impart permanent dark or intense colors to the hair in the absence of a peroxide or metal peroxide. Color is generated in the presence of atmospheric oxygen. 3-Methyl-1-phenyl-2-pyrazolin-5-one is mentioned as one of the couplers to vary the shade of the hair.

U.S. Pat. No. 4,169,703 covers a composition useful for dyeing keratinous fiber red without using o-, m-, p-phenylenediamine, 2,4-diaminoanisole or nitro compounds. In this patent, 3-methyl-1-phenyl-2-pyrazolin-5-one is described as an antioxidant.

U.S. Pat. No. 4,003,699 describes oxidation hair dyes based upon tetraaminopyrimidine developers. 1-Phenyl-2-pyrazolin-5-one derivatives, including 3-methyl-1-phenyl-2-pyrazolin-5-one and 3-amino-1-phenyl-2-pyrazolin-5-one, have been disclosed as couplers. With tetraaminopyrimidine, they produce a wide range of colors ranging from brownish orange to red, brick red, tomato red and reddish brown.

DE 2,357,215 covers 2,3,4,6-tetraaminopyridine as a primary intermediate. It couples with 3-methyl-1-phenyl-2-pyrazolin-5-one and 3-amino-1-phenyl-2-pyrazolin-5-one to produce red brown and bloody red respectively.

3-Acetamino-1-phenyl-5-acetoxy-1H-pyrazole was reported in Bull. Soc. Chim. Fr. (1974, pages 291–293). However, its use as a hair dye was not appreciated by those skilled in the art.

SUMMARY OF THE INVENTION

It is an object of the invention to provide oxidative hair dye compositions comprising as primary dye intermediates 2,6-dichloro-4-aminophenol, 2-chloro-4-aminophenol, or a mixture thereof, and 3-methyl-1-phenyl-2-pyrazolin-5-one, 3-amino-1-phenyl-2-pyrazolin-5-one, 3-acetamino-1-phenyl-5-acetoxy-1H-pyrazole, or a mixture thereof as coupling agents, oxidizing agents and other adjuvant substances and methods for the oxidative dyeing of hair employing such compositions.

The present invention relates to a dyeing composition for dyeing keratinous fibers and in particular for human keratinous fibers comprising 4-amino-2,6-dichlorophenol (1) or 4-amino-2-chlorophenol (2) and 3-methyl-1-phenyl-2-pyrazolin-5-one (3) or 3-amino-1-phenyl-2-pyrazolin-5-one (4) or 3-acetamino-1-phenyl-5-acetoxy-1H-pyrazole (5) and a dyeing process using such combination.

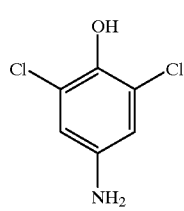
(1)

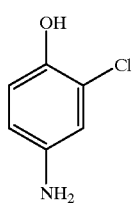
(2)

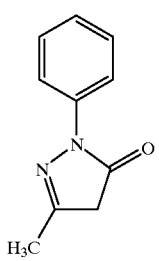
(3)

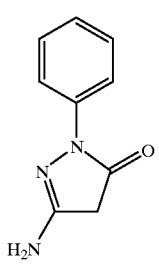
(4)

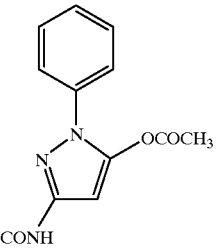
(5)

DETAILED DESCRIPTION OF THE INVENTION

4-Amino-2,6-dichlorophenol (1) and 4-amino-2-chlorophenol (2) are considered typical developers. 3-Methyl-1-phenyl-2-pyrazolin-5-one and 3-amino-1-phenyl-2-pyrazolin-5-one are known as photographic magenta couplers. Magenta dyes are produced when the magenta couplers react with quinone diamines derived from oxidation of p-phenylenediamine derivatives such as N-ethyl-N-(2-hydroxyethyl)-p-phenylenediamine (CD-4), N,N-diethyl-3-methyl-p-phenylenediamine monohydrochloride (CD2, Activol No. 2) and N,N-diethyl-p-phenylenediamine monohydrochloride (CD1).

The usefulness of formulations using (1) or (2) in combination with magenta couplers to oxidative hair coloring was not appreciated in the prior art prior to the present invention.

When hair was dyed, under oxidative conditions with a mixture of 4-aminophenol, 4-amino-3-methylphenol or 4-amino-2,6-dimethylphenol and pyrazolone couplers, as described above, very little color was developed in the hair fibers.

It has been surprisingly found that 4-amino-2,6-dichlorophenol (1) couples well with 3-methyl-1-phenyl-2-pyrazolin-5-one (3) to color hair red (Table 1, A compositions). This red color is very unique. Thus, the compounds of the invention considerably increase the possibilities for formulating varying shades without relying on p-phenylenediamine. 3-Amino-1-phenyl-2-pyrazolin-5-one (4), and 3-acetamino-1-phenyl-5-acetoxy-1H-pyrazole (5) color hair orange-red and red violet, respectively (see Table 1, B composition infra).

4-Amino-2-chlorophenol (2) couples with 3-amino-1-phenyl-2-pyrazolin-5-one (4), 3-methyl-1-phenyl-2-pyrazolin-5-one (3) and 3-acetamino-1-phenyl-5-acetoxy-1H-pyrazole (5) to produce orange, orange-red and red respectively (see Table 1, C composition infra).

The hair color obtained from 4-amino-2,6-dichlorophenol (1) and 3-methyl-1-phenyl-2-pyrazolin-5-one (3) is very similar to that of hair dyed with p-phenylenediamine and 5-amino-2-methylphenol. This finding allows one to formulate dark red and burgundy shades without relying on p-phenylenediamine. For example, a combination of 4-aminophenol, 4-amino-2,6-dichlorophenol, 5-amino-2-methylphenol and 3-methyl-1-phenyl-2-pyrazolin-5-one colors hair red plum (see Table 2, D composition infra).

The usefulness of the present invention is demonstrated by formulating a neutral dark blond shade with conventional primary intermediate and couplers (see Table 2, E composition infra).

In addition to at least one of the dye molecules encompassed by the present invention, the hair dyeing compositions described herein may also contain at least one other known and usual dye ingredient (i.e., used as primary dye intermediates and/or couplers), as well as conventional direct-dyes in admixture, should these substances be necessary or desired for the development and production of certain color nuances and tints.

Illustrative component dye ingredients that are conventionally admixed and employed as constituents of customary hair dye formulations and that can be considered suitable for use in the compositions of the present invention are set forth hereinbelow.

Included among the possible dye components that may be considered for use as primary intermediates and/or couplers in the dye compositions of the present invention are the following: p-phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis-hydroxyethyl-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis(2-hydroxyethyl)-N,N-bis(4-aminophenyl)-2-propanol; and 2-methyl-4-dimethylaminoaniline, or combinations thereof.

Preferred p-phenylenediamine derivatives include: p-toluenediamine; p-phenylenediamine; N-2-methoxyethyl-p-phenylenediamine; N,N-bis-hydroxyethyl-p-phenylenediamine; and 2-hydroxyethyl-p-phenylenediamine.

p-Aminophenol derivatives include: p-aminophenol; p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; and 5-aminosalicylic acid, or combinations thereof.

Preferred p-aminophenol derivatives include: p-aminophenol; p-methylaminophenol; 3-methyl-p-aminophenol; 2-methyl-p-aminophenol; 2-(2'-hydroxyethylaminomethyl)-p-aminophenol; 2-methoxymethyl-p-aminophenol; and 5-aminosalicylic acid.

Ortho developers include: catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol, or combinations thereof.

Preferred ortho developers include: o-aminophenol; 2,4-diaminophenol; 2,4,5-trihydroxytoluene; 1,2,4-trihydroxybenzene; 2-ethylamino-p-cresol; 5-methyl-o-aminophenol; 6-methyl-o-aminophenol; and 2-amino-5-acetaminophenol.

Phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid, or combinations thereof.

Preferred phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol; thymol (2-isopropyl-5-methylphenol); and 2,3-dihydroxy-1,4-naphthoquinone. m-Phenylenediamines include: m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4-hydroxyethylaminoanisole; 1-aminoethoxy-2,4-diaminobenzene; 2,4-diaminophenoxyacetic acid; 4,6-bis(2-hydroxyethoxy)-m-phenylenediamine; 2,4-diamino-5-methylphenetole; 2,4-diamino-5-hydroxyethoxytoluene; 2,4-dimethoxy-1,3-diaminobenzene; and 2,6-bis(hydroxyethylamino) toluene, or combinations thereof.

Preferred m-phenylenediamines include: m-phenylenediamine; 2-(2,4-diaminophenoxy)ethanol; N,N-bis(2,4-diaminophenoxy)-1,3-propane; 1-hydroxyethyl-2,4-diaminobenzene; 2-amino-4-hydroxyethylamino anisole; 4,6-bis(hydroxyethoxy)-m-phenylenediamine; 2,4-diamino-5-methylphenetole; 2,4-diamino-5-hydroxyethoxytoluene; 2,4-dimethoxy-1,3-diaminobenzene; and 2,6-bis(hydroxyethylamino)toluene.

m-Aminophenols include: m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethyloxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol, or combinations thereof.

Preferred m-aminophenols include: m-aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol.

Heterocyclic derivatives include: 2-dimethylamino-5-aminopyridine; 2,4,5,6-tetra-aminopyrimidine; 4,5-diamino-1-methyl-pyrazole; 1-phenyl-3-methyl-5-pyrazolone; 6-methoxy-8-aminoquinoline; 2,6-dihydroxy-4-methylpyridine; 5-hydroxy-1,4-benzodioxan; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(hydroxyethyloxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Preferred heterocyclic derivatives include: 4,5-diamino-1-methylpyrazole; 2-dimethylamino-5-aminopyridine; 2,4, 5,6-tetra-aminopyrimidine; 1-phenyl-3-methyl-5-pyrazolone; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 4-hydroxyindole; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine.

The additional dye compounds, e.g., couplers, should be present in the hair dyeing compositions of the present invention in an amount of approximately 0.01 to 10%, by weight, preferably approximately 0.1 to 5%, by weight, based on the total weight of the composition. Before mixing of the color precursos with the oxidative developer, the total quantity of the primary intermediate(s) and coupler(s) in the composition suitably amounts to approximately 0.1 to 10%, by weight, and preferably, approximately 0.5 to 5% by weight, based on the total weight of the composition.

Unless indicated otherwise, as used herein, reagent or component amounts are in % by weight (w/w), based on the total weight of the composition.

In the compositions of the present invention, the coupler(s) is generally used in approximately equimolar amounts relative to the primary intermediate(s). However, it will be appreciated that the primary intermediate(s), in relation to the coupler(s), may be present either in increased or decreased amounts depending upon the formulation and the desired color, intensity or effect. In general terms, the primary intermediate(s) and coupler(s), or cosmetically acceptable salts thereof, will be present in amounts such that in the presence of the oxidizing developer they produce a tinctorially effective amount of oxidative hair dye to color a hair fiber.

The hair dye preparations of the present invention may be formulated into cosmetic preparations such as a solution, cream, lotion, gel or emulsion. Also, in accordance with the invention, the compositions may represent a mixture of the coloring components (i.e., primary intermediate(s) and coupler(s)) with other components commonly associated with the formulation of solutions, creams, lotions, gels or emulsions, and the like. For example, components such as wetting agents or emulsifying agents from the categories of anionic or non-ionic surfactants, such as sulfates of fatty alcohols, alkanolamides of fatty alcohols, alkyl sulfonates, alkylbenzene sulfonates, oxyethylated fatty alcohols, oxyethylated nonylphenols. Thickeners, such a fatty alcohols, starch, cellulose derivatives, paraffin oil and fatty acids, as well as hair-care substances such as lanolin derivatives, cholesterol and pantothenic acid, may also be formulated into the compositions of the invention.

As an example, if formulated as a lotion, the compositions of the invention may contain organic solvents to assist in dissolving the dye precursors. Accordingly, the organic solvent content of the lotion may be from 0% to about 20%, preferably, about 1% to about 15%. Typically useful solvents include alcohols containing up to three carbon atoms such as ethanol and isopropanol, polyhydroxy alcohols such as propylene or hexylene glycol and lower alkyl ethers thereof, such as ethoxy ethers e.g. ethoxy diglycol.

In addition, the hair dyeing compositions in accordance with the present invention may optionally contain conventionally-used adjuvants and cosmetic additives, or mixtures thereof, to achieve the final formulations. Examples of such additives include, but are not limited to, anti-oxidants, e.g., ascorbic acid, erythorbic acid, or sodium sulfite, to inhibit premature oxidizing; fragrances and/or perfume oils; chelating agents; emulsifiers; coloring agents; thickeners; organic solvents; opacifying agents; dispersing agents; sequestering agents; hair-care substances; humectants; and anti-microbials, and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, *Cosmetics: Science and Technology*, Vol. 2, Second Edition, (1972).

Thickeners that may be used in the compositions of the present invention include a variety of fatty acid soaps and associative polymeric thickeners. The fatty acid soaps are alkali metal salts or alkanolamine salts of $C_{10}$–$C_{18}$ fatty acids. The preferred fatty acids include oleic acid, myristic acid and lauric acid, which are generally present in the compositions of the invention at about 0.5% to about 20%, preferably about 1% to about 10%. Associative thickeners are polymers that can thicken solutions at low concentrations. Among the associative thickeners that are useful in the compositions of the present invention are acrylates copolymer (sold by Rohm and Haas under the tradename Aculyn-33), ceteareth-20 acrylates/steareth-20 methacrylate copolymer (sold by Rohm and Haas under the Trade Name Aculyn-22), acrylates/steareth-20 itaconate copolymer and acrylates/ceteth-20 itaconate copolymer. Another class of associative thickeners that is useful in the compositions of the present invention include the copolymers of polyurethane and polyethylene glycol or polyether urethanes. One such material is sold by Rohm and Haas under the tradename Aculyn-44. The associative polymeric thickeners are generally present in the compositions of the invention at about 0.1% to about 10%, preferably, about 0.5% to about 5%.

The oxidative coupling, i.e., the development of the dye, to produce the final color product on the hair, can, in principle, be performed with atmospheric oxygen. However, chemical oxidizing agents are suitably and preferably used. Although other oxidizing agents can be employed, hydrogen peroxide is a preferred oxidizing compound for use as a developer with the primary intermediate and coupler dye precursors of the invention. The concentration of hydrogen peroxide in the developer may be from about 1% to about 15%, preferably, from about 3% to about 12%. Other suitable oxidizing agents include, for example, urea peroxide, melamine peroxide, perborates and percarbonates such as sodium perborate or percarbonate. The amounts of such oxidizing agents can be routinely determined by one having skill in the art, without requiring any inventive skill.

The compositions of the invention may include a typical anionic, cationic, nonionic or amphoteric surfactant. The anionic surfactants include the variety of alkyl sulfates, alkylether sulfates, alkyl sulfonates, alkyl sulfosuccinates and N-acyl sarcosinates. The commonly-used anionic surfactants are sodium and ammonium lauryl sulfates, sodium and ammonium laureth sulfate and alpha olefin sulfonates. Anionic surfactants are generally present in the compositions of the present invention at about 0.1% to about 15%, preferably, about 0.5% to about 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauramide diethanolamide; lauramide monoethanolamide; isopropyl palmitate, isopropyl stearate and decylpolyglucoside. Nonionic surfactants are generally present in the compositions of the present invention at about 0.1% to about 15%, preferably, about 0.5% to about 10%.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to about 10%, preferably, about 0.5% to about 5%.

Amphoteric surfactants that can be incorporated in the compositions of the present invention belong to the class of surface active chemicals that possess a positive and a negative charge in the same molecule and behave as a cation, an anion, or both, depending upon the pH of the medium and the nature of the amphoteric molecule. In general, the positive charge is located on a nitrogen, while the negative charge is carried by a carboxyl or sulfonate group. There are a large number of amphoteric surfactants that are suitable for use in the present invention, including, for example, the well-known betaines, sultaines, glycinates and propionates that may generally be represented by the following structural formulae shown below:

1. Betaines:

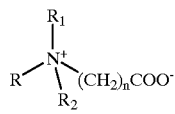

2. Sultaines:

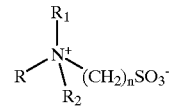

3. Propionates:

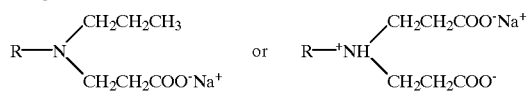

4. Glycinates:

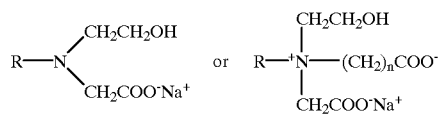

In these formulae, R is an alkyl or alkylamide group containing from about 10 to about 20 carbon atoms. $R_1$ and $R_2$ are alkyl or hydroxyalkyl groups, which may be the same or different, and contain up to about five carbon atoms; n is a positive integer from one to about five.

The selection of the amphoteric surfactant or mixture of surfactants for use in the present compositions and methods is not critical. The surfactant may be selected from among those suggested above, or from any of a number of other known amphoteric surfactants. The amount of amphoteric surfactant in the compositions of the present invention is normally from about 0.5% to about 15%, preferably, about 2% to about 10%.

Depending on the final formulated preparation, the compositions in accordance with invention may be weakly acidic, neutral or alkaine. In particular, the pH of the prepared compositions can range from about 5 to about 11. Preferred is a pH range of about 8 to 10. Any of a wide variety of alkaline reagents can be used to adjust the pH of the hair coloring compositions. Such alkaline reagents include ammonium hydroxide, potassium or calcium hydroxide, sodium or potassium carbonate, sodium phosphate, sodium silicate, guanidine hydroxide, or any one of the alkylamines or alkanolamines, for example, ethylamine, triethylamine, ethanolamine, diethanolamine, aminomethyl propanol, aminomethyl propanediol and the like. The preferred alkaline reagents are ammonium hydroxide, sodium carbonate and ethanolamine. With the reagents listed above, the selected pH will generally be achieved if the composition contains an alkaline agent in an amount from about 0.1% to about 15%, preferably, about 0.5% to about 5%.

The application of the dyeing components is carried out by methods familiar to those in the art, for example, by mixing the hair dyeing preparation with an oxidant shortly before use, or at the time of applying the mixture onto the hair. On the hair, the compositions form a stable formulation with enough consistency and body to remain on the hair without dripping or running during the complete coloring period. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 5 to 45 minutes, preferably, approximately 10 to 30 minutes), the composition is washed from the hair with an ordinary water rinse followed by a shampoo. The application temperature is in the range of about 15° C. to 50° C.

The compositions of this invention may be separately provided in a kit or packaged form ready for mixing by the user, either professional or consumer, to initiate the dyeing process. The kit provided in accordance with this invention comprises containers for housing the developer and the dye precursors. In the most convenient form, there will be two containers, one containing the primary dye intermediate and coupler, e.g., as a lotion; the other containing the oxidizing agent, also called the developer or developing agent.

The method of the invention comprises applying the mixture to the hair to be colored and allowing it to remain in contact with the hair until the desired hair color has been attained, after which time the composition is removed from the hair as described above.

EXAMPLES

The examples as set forth herein are meant to exemplify the various aspects of carrying out the invention and are not intended to limit the invention in any way.

The following compositions are mixed with 100 g of 20 volume hydrogen peroxide. The resulting mixture is applied to gray hair and permitted to remain in contact with hair for 30 minutes. Thus dyed hair is then shampooed and rinsed with water and dried.

TABLE 1

Compositions of A, B and C

| | A Composition (%) | B Composition (%) | C Composition (%) |
|---|---|---|---|
| Cocamidopropyl betaine | 17 | 17 | 17 |
| Ethanolamine | 2 | 2 | 2 |
| Oleic Acid | 0.75 | 0.75 | 0.75 |
| Citric Acid | 0.1 | 0.1 | 0.1 |
| Ammonium hydroxide | 5.0 | 5.0 | 5.0 |
| Behentrimonium chloride | 0.5 | 0.5 | 0.5 |
| Sodium sulfite | 0.1 | 0.1 | 0.1 |
| EDTA | 0.1 | 0.1 | 0.1 |
| Erythorbic acid | 0.4 | 0.4 | 0.4 |
| 4-Amino-2,6-dichlorophenol (1) | 0.89 | 0.89 | |
| 4-Amino-2-chlorophenol (2) | | | 0.72 |
| 3-Methyl-1-phenyl-2-pyrazolin-5-one (3) | 0.87 | | 0.87 |
| 3-Acetamino-1-phenyl-5-acetoxy-1H-pyrazole (5) | | 1.09 | |
| Water | QS 100 | QS 100 | QS 100 |
| Color | Red | Red Violet | Orange Red |

TABLE 2

Compositions of D and E

| | D Composition (%) | E Composition (%) |
|---|---|---|
| Cocamidopropyl betaine | 17 | 17 |
| Ethanolamine | 2 | 2 |
| Oleic Acid | 0.75 | 0.75 |
| Citric Acid | 0.1 | 0.1 |
| Ammonium hydroxide | 5.0 | 5.0 |
| Behentrimonium chloride | 0.5 | 0.5 |
| Sodium sulfite | 0.1 | 0.1 |
| EDTA | 0.1 | 0.1 |
| Erythorbic acid | 0.4 | 0.4 |
| 4-Aminophenol | 0.55 | 0.55 |
| 4-Amino-2,6-dichlorophenol (1) | 0.89 | 0.89 |
| 5-Amino-2-methylphenol | 0.62 | |
| 2-Methylresorcinol | | 0.62 |
| 3-Methyl-1-phenyl-2-pyrazolin-5-one (3) | 0.87 | 0.87 |
| Water | QS 100 | QS 100 |
| Shade | Red plum | Neutral dark blonde |

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. In a composition for the oxidative coloring of hair, said composition containing a primary intermediate and a coupler in a cosmetically acceptable vehicle, wherein said primary intermediate and said coupler form an oxidative hair dye in the presence of an oxidizing agent, the improvement comprising said primary intermediate is an aminophenol of the formula:

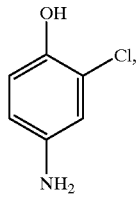

(2)

or a cosmetically acceptable salt thereof, and said coupler is a pyrazolone of the formula:

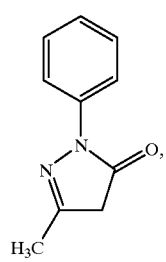

(3)

or a cosmetically acceptable salt thereof.

2. The composition according to claim 1, wherein said primary intermediate is present at about 0.1% to about 5%, by weight, based on the total weight of the composition.

3. The composition according to claim 1, wherein the coupler is present in an amount of about 0.1% to about 5%, by weight, based on the total weight of the composition.

4. The composition according to claim 1, further including one or more additional dye components selected from the group consisting of p-phenylenediamine and cosmetically acceptable derivatives thereof; p-aminophenols and cosmetically acceptable derivatives thereof; ortho developers and cosmetically acceptable derivatives thereof; phenols and cosmetically acceptable derivatives thereof; resorcinols and cosmetically acceptable derivatives thereof; m-phenylenediamines and cosmetically acceptable derivatives thereof; m-aminophenols and cosmetically acceptable derivatives thereof; and heterocyclic derivatives selected from the group consisting of 2-dimethylamino-5-aminopyridine; 2,4,5,6-tetra-aminopyrimidine; 4,5-diamino-1-methyl-pyrazole; 1-phenyl-3-methyl-5-pyrazolone; 6-methoxy-8-aminoguinoline; 2,6-dihydroxy-4-methylpyridine; 5-hydroxy-1,4-benzodioxan; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(hydroxyethyloxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, and mixtures thereof.

5. The composition according to claim 1, further including an oxidizing agent, whereby said oxidative hair dye is produced.

6. The composition according to claim 1, wherein said oxidizing agent is hydrogen peroxide.

7. A method for the oxidative coloring of human hair comprising contacting the hair with a hair coloring effective amount of the composition according to claim 1 in the presence of an oxidizing agent and maintaining contact with the hair until the hair is colored.

8. An oxidative hair dye product produced by reacting, in a cosmetically acceptable vehicle and in the presence of an oxidizing agent an aminophenol of the formula:

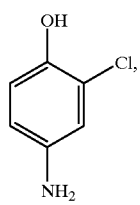

(2)

or a cosmetically acceptable salt thereof, and a pyrazolone of the formula:

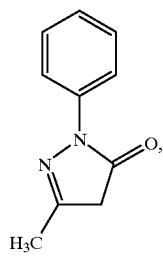

(3)

or a cosmetically acceptable salt thereof.

9. The hair dye products according to claim 8, further including at least one adjuvant selected from the group consisting of wetting agents, emulsifying agents, thickeners, organic solvents, antioxidants, chelating agents, opacifying agents, humectants, hair conditioning agents, preservatives and perfumes.

10. In a composition for the oxidative coloring of hair, said composition containing a primary intermediate and a coupler in a cosmetically acceptable vehicle, wherein said primary intermediate and said coupler form an oxidative hair dye in the presence of an oxidizing agent, the improvement comprising said primary intermediate is an aminophenol of the formula:

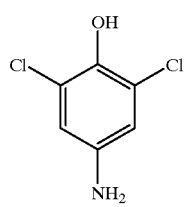

(1)

or a cosmetically acceptable salt thereof, and said coupler is a pyrazolone of the formula:

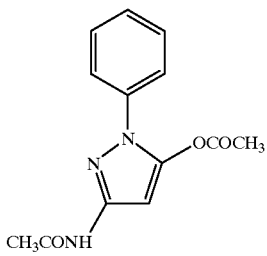

(5)

or a cosmetically acceptable salt thereof.

11. In a composition for the oxidative coloring of hair, said composition containing a primary intermediate and a coupler in a cosmetically acceptable vehicle, wherein said primary intermediate and said coupler form an oxidative hair dye in the presence of an oxidizing agent, the improvement comprising said primary intermediate is an aminophenol of the formula:

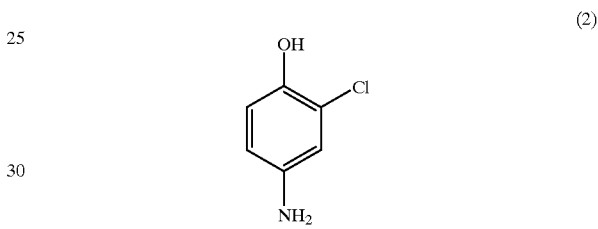

(2)

or a cosmetically acceptable salt thereof, and said coupler is a pyrazolone of the formula:

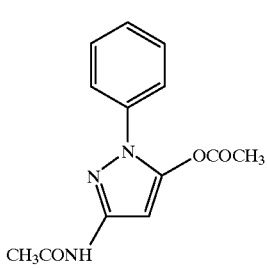

(5)

or a cosmetically acceptable salt thereof.

12. An oxidative hair dye product produced by reacting, in a cosmetically acceptable vehicle and in the presence of an oxidizing agent, an aminophenol of the formula:

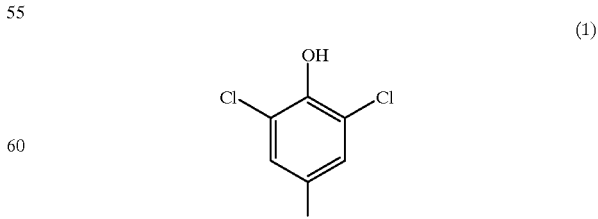

(1)

or a cosmetically acceptable salt thereof, and a pyrazolone of the formula:

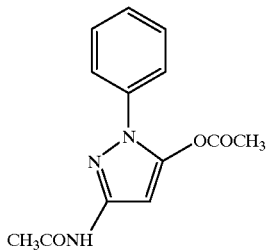

or a cosmetically acceptable salt thereof.

13. An oxidative hair dye product produced by reacting, in a cosmetically acceptable vehicle and in the presence of an oxidizing agent, an aminophenol of the formula:

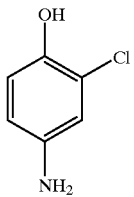

or a cosmetically acceptable salt thereof, and a pyrazolone of the formula:

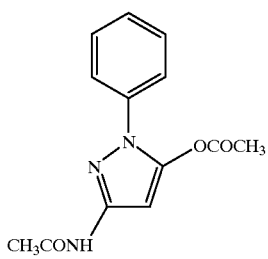

or a cosmetically acceptable salt thereof.

14. The composition according to claim 10, wherein said primary intermediate is present at about 0.1% to about 5%, by weight, based on the total weight of the composition.

15. The composition according to claim 11, wherein said primary intermediate is present at about 0.1% to about 5%, by weight, based on the total weight of the composition.

16. The hair dye product according to claim 12, further including at least one adjuvant selected from the group consisting of wetting agents, emulsifying agents, thickeners, organic solvents, antioxidants, chelating agents, opacifying agents, humectants, hair conditioning agents, preservatives and perfumes.

17. The hair dye product according to claim 13, further including at least one adjuvant selected from the group consisting of wetting agents, emulsifying agents, thickeners, organic solvents, antioxidants, chelating agents, opacifying agents, humectants, hair conditioning agents, preservatives and perfumes.

18. The composition according to claim 10, further including one or more additional dye components selected from the group consisting of p-phenylenediamine and cosmetically acceptable derivatives thereof; p-aminophenols and cosmetically acceptable derivatives thereof; ortho developers and cosmetically acceptable derivatives thereof; phenols and cosmetically acceptable derivatives thereof; resorcinols and cosmetically acceptable derivatives thereof; m-phenylenediamines and cosmetically acceptable derivatives thereof; m-aminophenols and cosmetically acceptable derivatives thereof; and heterocyclic derivatives selected from the group consisting of 2-dimethylamino-5-aminopyridine; 2,4,5,6-tetra-aminopyrimidine; 4,5-diamino-1-methyl-pyrazole; 1-phenyl-3-methyl-5-pyrazolone; 6-methoxy-8-aminoquinoline; 2,6-dihydroxy-4-methylpyridine; 5-hydroxy-1,4-benzodioxan; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(hydroxyethyloxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, and mixtures thereof.

19. The composition according to claim 11, further including one or more additional dye components selected from the group consisting of p-phenylenediamine and cosmetically acceptable derivatives thereof; p-aminophenols and cosmetically acceptable derivatives thereof; ortho developers and cosmetically acceptable derivatives thereof; phenols and cosmetically acceptable derivatives thereof; resorcinols and cosmetically acceptable derivatives thereof; m-phenylenediamines and cosmetically acceptable derivatives thereof; m-aminophenols and cosmetically acceptable derivatives thereof; and heterocyclic derivatives selected from the group consisting of 2-dimethylamino-5-aminopyridine; 2,4,5,6-tetra-aminopyrimidine; 4,5-diamino-1-methyl-pyrazole; 1-phenyl-3-methyl-5-pyrazolone; 6-methoxy-8-aminoquinoline; 2,6-dihydroxy-4-methylpyridine; 5-hydroxy-1,4-benzodioxan; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(hydroxyethyloxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-brono-4,5-methylenedioxyphenol; 6-hydroxyindole; 3-amino-2-methylamino-6-methoxypyridine; $_2$-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, and mixtures thereof.

20. The composition according to claim 10, further including an oxidizing agent, whereby said oxidative hair dye is produced.

21. The composition according to claim 11, further including an oxidizing agent, whereby said oxidative hair dye is produced.

22. The composition according to claim 10, wherein said oxidizing agent is hydrogen peroxide.

23. The composition according to claim 11, wherein said oxidizing agent is hydrogen peroxide.

24. A method for the oxidative coloring of human hair comprising contacting the hair with a hair coloring effective amount of the composition according to claim 10 in the presence of an oxidizing agent and maintaining contact with the hair until the hair is colored.

25. A method for the oxidative coloring of human hair comprising contacting the hair with a hair coloring effective amount of the composition according to claim 11, in the presence of an oxidizing agent and maintaining contact with the hair until the hair is colored.

* * * * *